United States Patent
Deaver et al.

(10) Patent No.: US 10,758,527 B2
(45) Date of Patent: *Sep. 1, 2020

(54) OPIOID AGONIST ANTAGONIST COMBINATIONS

(71) Applicant: Alkermes Pharma Ireland Limited, Dublin (IE)

(72) Inventors: Daniel Deaver, Franklin, MA (US); Elliot Ehrich, Boston, MA (US)

(73) Assignee: Alkermes Pharma Ireland Limited, Dublin (IE)

(*) Notice: Subject to any disclaimer, the term of this patent is extended or adjusted under 35 U.S.C. 154(b) by 26 days.

This patent is subject to a terminal disclaimer.

(21) Appl. No.: 16/219,083

(22) Filed: Dec. 13, 2018

(65) Prior Publication Data
US 2019/0192505 A1    Jun. 27, 2019

Related U.S. Application Data (63) Continuation of application No. 14/941,867, filed on Nov. 16, 2015, now Pat. No. 10,195,191, which is a
(Continued)

(51) Int. Cl.
A61K 31/4748    (2006.01)
A61K 31/485     (2006.01)
(Continued)

(52) U.S. Cl.
CPC ........ *A61K 31/4748* (2013.01); *A61K 31/135* (2013.01); *A61K 31/137* (2013.01);
(Continued)

(58) Field of Classification Search
None
See application file for complete search history.

(56) References Cited

U.S. PATENT DOCUMENTS

| | | |
|---|---|---|
| 5,512,593 A | 4/1996 | Dante |
| 2003/0181475 A1 | 9/2003 | Sanchez et al. |

(Continued)

FOREIGN PATENT DOCUMENTS

| | | |
|---|---|---|
| WO | 2013088242 A1 | 6/2013 |
| WO | WO-2013088242 A1 * | 6/2013 |

OTHER PUBLICATIONS

"Alkermes Initiates Clinical Study of ALKS 5461 for Treatment-Resistant Depression", Business Wire, [retrieved on Jun. 5, 2015]. Retrieved from the Internet: < URL: http://www.businesswire.com/news/home/20110615005342/en/Alkermes-Initiates-Clinical-Study-ALKS-5461-Treatment-Resistant >. Jun. 15, 2011, [online], Jul. 15, 2011.

(Continued)

*Primary Examiner* — Savitha M Rao
*Assistant Examiner* — Andrew P Lee
(74) *Attorney, Agent, or Firm* — Elmore Patent Law Group, P.C.; Carolyn Elmore; Joseph Zucchero (57) ABSTRACT

The invention relates a composition comprising an opioid agonist and Compound-1:

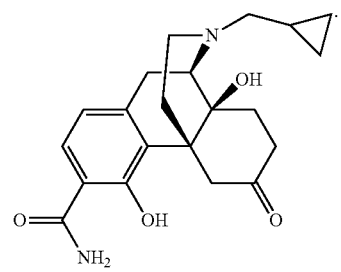

41 Claims, 6 Drawing Sheets

Related U.S. Application Data continuation of application No. 13/717,128, filed on Dec. 17, 2012, now Pat. No. 9,211,293, which is a continuation-in-part of application No. 13/715,518, filed on Dec. 14, 2012, now abandoned.

(60) Provisional application No. 61/576,233, filed on Dec. 15, 2011.

(51) Int. Cl.
| | |
|---|---|
| *A61K 45/06* | (2006.01) |
| *A61K 31/135* | (2006.01) |
| *A61K 31/137* | (2006.01) |
| *A61K 31/138* | (2006.01) |
| *A61K 31/15* | (2006.01) |
| *A61K 31/343* | (2006.01) |
| *A61K 31/4525* | (2006.01) |
| *A61K 31/496* | (2006.01) |

(52) U.S. Cl.
CPC ............ *A61K 31/138* (2013.01); *A61K 31/15* (2013.01); *A61K 31/343* (2013.01); *A61K 31/4525* (2013.01); *A61K 31/485* (2013.01); *A61K 31/496* (2013.01); *A61K 45/06* (2013.01)

(56) References Cited

U.S. PATENT DOCUMENTS

| | | |
|---|---|---|
| 2009/0311347 A1 | 12/2009 | Oronsky et al. |
| 2010/0240691 A1 | 9/2010 | Turncliff et al. |
| 2011/0136848 A1 | 6/2011 | Silverman |

OTHER PUBLICATIONS

"Alkermes: Alkermes Initiates Clinical Study of ALKS 5461 for Treatment-Resistant Depression", Retrieved from the Internet: URL: http://www.pipelinereview.com/index.php/2011061543028/Neurology-and-Psychiatry/A lkermes-Initiates-Clinical-Study-of-ALKS-5461-for-Treatment-Resistant-Depression.html [retrieved on Mar. 14, 2013], Jun. 15, 2011.

Alkermes: "Strong results for Alkermes' ALKS 5461 in major depressive disorder" Retrieved from the Internet: URL:http://www.thepharmaletter.com/file/109997/strong-results-for-alkermes-alks-5461-in-major-depressive-disorder.html [retrieved on Mar. 14, 2013], Jan. 4, 2012.

Ayumi, Igaku N., Process of Medicine, 137(7),1986, 523-524.

Ayumi, Igaku N., Process of Medicine, 219(13), Dec. 30, 2006, 893-897.

Ayumi, Igaku N., Process of Medicine, 210(11), Sep. 11, 2004, 943-960.

Kasai, et al., "Genes and Functions of Opioid Peptide Receptors", Journal of Pharmacological Science, 130, 2007, 235-237.

Taketa, Y., "Opioids, Nihon Rinsho", Japan Clinical Medicine, 68, 2010, 455-459.

* cited by examiner

OPIOID AGONIST ANTAGONIST COMBINATIONS

RELATED APPLICATIONS

This application is a continuation of U.S. application Ser. No. 14/941,867, filed Nov. 16, 2015, which is a continuation of U.S. application Ser. No. 13/717,128, filed Dec. 17, 2012, now U.S. Pat. No. 9,211,293, issued Dec. 15, 2015, which is a continuation-in-part of U.S. application Ser. No. 13/715,518, filed Dec. 14, 2012, now abandoned, which claims the benefit of U.S. Provisional Application 61/576,233, filed Dec. 15, 2011. The entire teachings of the above applications are incorporated herein by reference.

BACKGROUND

Opioids produce both analgesia and euphoria. The mood altering action of opioids in addition to the physical dependence and addictive qualities of this class of drugs encourages abuse. Both chronic pain and prescription opioid abuse are prevalent and continue to exact a heavy toll on patients, physicians, and society. Individuals with chronic pain and co-occurring substance use disorders and/or mental health disorders, are at a higher risk for misuse of prescribed opioids. Treatment approaches that balance treating chronic pain while minimizing risks for opioid abuse, misuse, and diversion are much needed. [Sehgal N. et al., Pain Physician 2012; 15, 2150-1149].

The opioid neuropeptide system plays an important part in regulating mood disorders. [Machado-Viera R. et al.; Depression and Anxiety, 28 (4) 2011, 267-281]. Opioid peptides and their receptors are potential candidates for the development of novel antidepressant treatment. The actions of endogenous opioids and opiates are mediated by three receptor types (µ, δ and κ), which are coupled to different intracellular effector systems. [Berrocoso E. et al., Current Pharmaceutical Design, 15(14) 2009, 1612-22]. As such, agents that can modulate the actions of one or more of the opioid receptor types with selectivity and sensitivity are important to treat the various diseases and disorders regulated by the opioid system.

While opioid agonists have anti-depressant effects they are generally not used to treat depression. Long-term use of a µ-opioid agonist may result in the development of opioid-dependency in patients. In addition there are other undesirable side effects including additive potential, sedation, respiratory depression, nausea and constipation that will accompany acute and chronic opioid use. Buprenorphine is a µ-opioid partial agonist which produces typical µ-opioid agonist effects and side effects such as additive potential and respiratory depression while producing maximal effects that are less than those of full agonists like heroin and methadone. At low doses buprenorphine produces sufficient µ-agonist effect to enable opioid-addicted individuals to discontinue the misuse of opioids without experiencing withdrawal symptoms.

While there are many well-known opioid receptor binding compounds, there is little evidence to guide the management of depression that has not responded to a course of antidepressants. Treatment-refractory depression is an important public health problem and large pragmatic trials are needed to inform clinical practice. [Stimpson et al., The British Journal of Psychiatry, (2002) 181: 284-294]. There still remains a need to develop effective treatments of mood disorders, in particular major depressive disorders.

SUMMARY OF THE INVENTION

The invention relates to a composition comprising pharmaceutically effective amounts of an opioid agonist and Compound-1:

The invention further provides a method for treating an opioid receptor mediated disease or disorder comprising the step of administering a composition comprising Compound-1 and an opioid agonist. The invention further provides a dosage form comprising pharmaceutically effective amounts of Compound-1 and an opioid agonist.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The invention relates to a composition comprising pharmaceutically effective amounts of an opioid agonist and Compound-1:

The invention further provides a method for treating an opioid receptor mediated disease or disorder comprising the step of administering a composition comprising Compound-1 and an opioid agonist. The invention further provides a dosage form comprising pharmaceutically effective amounts of Compound-1 and an opioid agonist.

The invention further provides a composition comprising Compound-1 and an opioid agonist wherein the molar ratio of Compound-1:agonist is about 0.5-5.0:1.0, or about 0.5-4.0:1.0, or about 0.5-3.0:1.0, or about 0.5-2.5:1.0, or about 0.5-1.75:1.0, or about 0.75-1.5:1.0, or about 0.9-1.3:1.0. The invention further provides an oral dosage form comprising a pharmaceutically effective amount of an opioid agonist and Compound-1 wherein the molar ratio of Compound-1:agonist is about 0.5-5.0:1.0, or about 0.5-4.0:1.0, or about 0.5-3.0:1.0, or about 0.5-2.5:1.0, or about 0.5-1.75:1.0, or about 0.75-1.5:1.0, or about 0.9-1.3:1.0. The invention further provides a controlled release formulation comprising Compound-1 and an opioid agonist.

The invention relates to a method of treating pain comprising the step of administering a pharmaceutically effective amount of Compound-1 in combination with a pharmaceutically effective amount of an opioid agonist to a patient in need thereof.

The invention further relates to a method of treating a depressive disorder comprising the step of administering Compound-1 in combination with a partial opioid agonist to a patient in need thereof.

In one embodiment, the opioid agonist is other than a partial agonist. In one embodiment, the opioid agonist is a compound other than buprenorphine. In one embodiment, the partial agonist is a compound other than buprenorphine.

In one embodiment, the opioid agonist is a partial agonist at μ-opioid receptor (partial agonist). In one embodiment, the partial agonist is selected from butorphanol, dezocine, nalbulphine, pentazocine and buprenorphine. In one embodiment, the composition further comprises an additional agent for the treatment of depression such as a selective serotonin re-uptake inhibitor, serotonin reuptake inhibitor (SSRI), serotonin-norepinephrine reuptake inhibitor (SNRI), monoamine oxidase inhibitor (MAOIs) and tricyclic antidepressants, or an antidepressant compound belonging to the heterocyclic class. In one embodiment, the additional anti-depressant is selected from fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, milnacipran, femoxetine and alaproclate.

In one embodiment, the invention relates to the treatment of depressive disorder comprising the step of administering Compound-1 in combination with a partial opioid agonist to a patient in need thereof. In one embodiment, the partial opioid agonist is a compound other than buprenorphine. In one embodiment, the depressive disorder is selected from major depressive disorder, chronic depression, severe unipolar recurrent major depressive episodes, dysthymic disorder, depressive neurosis and neurotic depression, melancholic depression, atypical depression, reactive depression, treatment resistant depression, seasonal affective disorder and pediatric depression; premenstrual syndrome, premenstrual dysphoric disorder, hot flashes, bipolar disorders or manic depression, bipolar I disorder, bipolar II disorder and cyclothymic disorder. In a preferred embodiment, the disorder is major depressive disorder. In one embodiment, the major depressive disorder is resistant to two or more antidepressants, for example, antidepressants such as selective serotonin reuptake inhibitors (SSRIs), Serotonin-norepinephrine reuptake inhibitors (SNRIs), Monoamine oxidase inhibitors (MAOIs) and Tricyclic antidepressants. In one embodiment, the disorder is treatment resistant depression. In one embodiment, the subject exhibits one or more depressive symptoms selected from irritability, feelings of hopelessness and helplessness, inability to concentrate, sadness, insomnia, appetite loss, lack of interest in life's activities, thoughts of suicide, dizziness, nausea, vomiting, hyperhidrosis, menorrhagia, pain in extremity, constipation, sedation, fatigue, feeling abnormal, flushing and somnolence. In one embodiment, the administration of said composition results in a release of between about 1 pg/sample to about 2 pg/sample of dopamine. In one embodiment, the molar ratio of Compound-1:agonist is about 0.5-5.0:1.0, or about 0.5-4.0:1.0, or about 0.5-3.0:1.0, or about 0.5-2.5:1.0, or about 0.5-1.75:1.0, or about 0.75-1.5:1.0, or about 0.9-1.3:1.0. In one embodiment the opioid agonist is other than a partial agonist. In one embodiment, the partial agonist is a compound other than buprenorphine.

Without being bound to any particular theory, it is postulated that the administration of some of the compositions of the invention may result in the modulation of the dopamine efflux. In one embodiment, administration of the composition results in dopamine efflux in the Nucleus Accumbens shell (NAc-sh) region of the mesolimbic region of the brain of between about 1 pg/sample to about 10 pg/sample of dopamine, between about 1 pg/sample to about 5 pg/sample, or between about 1 pg/sample to about 2 pg/sample of dopamine. The dopamine efflux modulation can be determined by the methods described herein (Example 2).

In one embodiment, the invention relates to a composition comprising a pharmaceutically effective amount of Compound-1 and an opioid agonist wherein upon administration of said composition to a patient for the treatment of pain said administration results in the reduction of dopamine release by about 10% to about 60% in comparison to dopamine release upon administration of the agonist alone, wherein said dopamine release is measured two hours after administering said composition. In one embodiment, the reduction of dopamine release is between about 20% to about 40% or between about 25% to about 35%.

In one embodiment, the administration of the composition of an agonist in combination with Compound-1 results in the reduction of visual analog scale (VAS) score for "feeling high" of between about 20% to about 60% in comparison with the administration of the agonist alone. In one embodiment, the reduction in VAS score is between about 25% to about 55% or between about 30% to about 50%. In one embodiment, the VAS score is reduced between about 20% to about 60% while the dopamine release is between about 1 pg/sample to about 10 pg/sample.

In one embodiment, the opioid agonist is selected from alfentanil, allylprodine, alphaprodine, anileridine, benzylmorphine, bezitramide, brifentanil, carfentanil, clonitazene, codeine, dextromoramide, desomorphine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, fentanyl, heroin, hydrocodone, hydrocodeine, hydromorphone, hydroxypethidine, isomethadone, ketobemidone, levorphanol, levallorphan, levomethadone, levophenacylmorphan, lofentanil, meperidine (pethidine), metazocine, methadone, metopon, 4-methoxymethylfentanyl, 3-methylfentanil, mirfentanil, 6-monoacetylmorphine, morphine, morphine-6-glucuronide, ohmefentanyl, oxycodone, oxymorphone, propoxyphene, pentazocine, propiram, propoxyphene, racemorphan, sufentanil, tapentadol, tramadol, tilidine.

In a preferred embodiment, the opioid agonist is selected from morphine, codeine, hydromorphone, hydrocodone, oxycodone, oxymorphone, dihydrocodeine, dihydromorphine and tramadol. In one embodiment, the molar ratio of Compound-1:agonist is about 0.5-5.0:1.0, or about 0.5-4.0:1.0, or about 0.5-3.0:1.0, or about 0.5-2.5:1.0, or about 0.5-1.75:1.0, or about 0.75-1.5:1.0, or about 0.9-1.3:1.0 wherein said agonist is selected from morphine, codeine, hydromorphone, hydrocodone, oxycodone, oxymorphone, dihydrocodeine, dihydromorphine and tramadol.

The invention further provides a method for treating an opioid receptor mediated disease or disorder comprising the step of administering a composition comprising Compound-1 and an opioid agonist. In one embodiment, the opioid receptor mediated disease or disorder is pain. In one embodiment the disease or disorder is selected from the group consisting of moderate to severe cancer pain, moderate to severe post-surgical pain, pain following physical trauma, pain associated with cardiac infarction and inflammatory pain.

In one embodiment, the invention relates to the treatment of pain wherein the opioid agonist is selected from alfentanil, allylprodine, alphaprodine, anileridine, benzylmorphine, bezitramide, brifentanil, carfentanil, clonitazene, codeine, dextromoramide, desomorphine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, fentanyl, heroin, hydrocodone, hydrocodeine, hydromorphone, hydroxypethidine, isomethadone, ketobemidone, levorphanol, levallorphan, levomethadone, levophenacylmorphan, lofentanil, meperidine (pethidine), metazocine, methadone, metopon, 4-methoxymethylfentanyl, 3-methylfentanil, mirfentanil, 6-monoacetylmorphine, morphine, morphine-6-glucuronide, ohmefentanyl, oxycodone, oxymorphone, propoxyphene, pentazocine, propiram, propoxyphene, racemorphan, sufentanil, tapentadol, tramadol, tilidine.

In a preferred embodiment, the invention relates to the treatment of pain wherein the opioid agonist is selected from morphine, codeine, hydromorphone, hydrocodone, oxycodone, oxymorphone, dihydrocodeine, dihydromorphine and tramadol.

The terms "compound" "drug", and "prodrug" as used herein all include pharmaceutically acceptable salts, co-crystals, solvates, hydrates, polymorphs, enantiomers, diastereoisomers, racemates and the like of the compounds, drugs and prodrugs of the compounds listed herein.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing occurrence or recurrence of disease, delay or slowing of disease progression, amelioration of the disease state, and remission (whether partial or total).

As used herein, the term "major depressive disorder" (MDD) is used as that term is understood in art, and refers to a diagnosis that is guided by diagnostic criteria listed in Diagnostic and Statistical Manual of Mental Disorders, Fourth Edition (DSM-IV) or ICD-10, or in similar nomenclatures.

Patients suffering from "treatment resistant depression" include: (1) those who fail to respond to standard doses (i.e., significantly superior to placebo in double-blind studies) of antidepressants (such as a monoamine oxidase inhibitors (MAOIs), tricyclic antidepressants (TCAs), tetracyclic antidepressants (TeCAs), selective serotonin reuptake inhibitors (SSRIs), and serotonin-norepinephrine reuptake inhibitors (SNRIs)) administered continuously for a minimum duration of 6 weeks, and (2) those who fail to respond to standard doses of an antidepressant (such as a monoamine oxidase inhibitors (MAOIs), tricyclic antidepressants (TCAs), tetracyclic antidepressants (TeCAs), selective serotonin reuptake inhibitors (SSRIs), and serotonin-norepinephrine reuptake inhibitors (SNRIs)) (monotherapy) administered continuously for a minimum duration of 12 weeks. One criteria for determining whether a patient's depression is treatment resistant to an antidepressant is if a Clinical Global Impression-Improvement (CGI-I) score of 1 (very much improved) or 2 (much improved) is not achieved by the end of a 6, 8, or 12 week trial. The CGI-I scale is defined in Guy, W. (ed.): ECDEU Assessment Manual for Psychopharmacology, Revised, DHEW Pub. No. (ADM) 76-338, Rockville, Md., National Institute of Mental Health, 1976.

Patients suffering from "pain" include chronic pains, such as neuropathic pain, and post-operative pain, chronic lower back pain, cluster headaches, herpes neuralgia, phantom limb pain, central pain, dental pain, neuropathic pain, opioid-resistant pain, visceral pain, surgical pain, bone injury pain, pain during labor and delivery, pain resulting from burns, including sunburn, post-partum pain, migraine, angina pain, and genitourinary tract-related pain including cystitis, nociceptive pain or nociception.

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha-(α), beta-(β) and gamma-(γ) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is parenteral administration by injection.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® or OMEGAVEN®, or solution, in a nontoxic parenterally acceptable diluent or solvent, for example, as a solution in 1,3-butanediol. INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics is known in the art (see, for example U.S. Pat. No. 5,767,068 to VanDevanter et al., U.S. Pat. No. 5,508,269 to Smith et al., and WO 98/43650 by Montgomery).

EXAMPLES

Example 1

A randomized, double-blind, placebo-controlled study was conducted evaluating the safety and tolerability of a combination of buprenorphine with Compound-1. The study was conducted in 32 adults with major depressive disorder who had an inadequate response to antidepressant therapy. In this study, subjects received a once daily sublingual dose of placebo or Compound-1-BUP at dose ratios of 1:8 or 1:1 with corresponding escalating doses of 0.25:2 mg/0.5:4 mg and 4:4 mg/8:8 mg, respectively, for 7 days.

Among the most common adverse events were dizziness, nausea, vomiting, and sedation (all of which were reported more frequently by subjects in the 1:8 ratio group (Cohort A) versus subjects in the 1:1 ratio (Cohort B) or placebo groups). For example, while about 28.5% of Cohort A reported sedation or somnolence, only 7% of Cohort B reported sedation or somnolence. The occurrence of dizziness was also significantly higher in Cohort A (57%) compared to Cohort B (29%). A summary of the most common adverse events (i.e, those reported by ≥10% of subjects in any treatment group) is provided in Table A:

TABLE A

Comparison of most common adverse events (>10% in any group) between placebo, Cohort A and Cohort B

| Adverse Event Preferred Term (N, %) | Placebo (N = 4) | Cohort A (N = 14) | Cohort B (N = 14) |
|---|---|---|---|
| Dizziness | 0 | 8 (57) | 4 (29) |
| Nausea | 1 (25) | 4 (29) | 3 (21) |
| Vomiting | 0 | 4 (29)* | 2 (14)* |
| Hyperhidrosis | 1 (25) | 2 (14) | 0 |
| Menorrhagia | 1 (25) | 0 | 0 |
| Pain in extremity | 1 (25) | 0 | 1 (7) |
| Constipation | 0 | 2 (14) | 3 (21) |
| Sedation or somnolence | 0 | 4 (28.5) | 1 (7) |
| Fatigue | 0 | 2 (14) | 1 (7) |
| Feeling abnormal | 0 | 0 | 2 (14) |
| Flushing | 0 | 2 (14) | 0 |

*One subject from each active group discontinued due to vomiting.
Cohort A: 1:8 ratio of Compound 1:Buprenorphine (0.25 mg:2 mg for days 1 to 3 and 0.5 mg:4 mg for days 4 to 7)
Cohort B: 1:1 ratio of Compound 1:Buprenorphine (4 mg:4 mg for days 1 to 3 and 8 mg:8 mg for days 4 to 7).

Efficacy was measured by changes from baseline to Day 7 in the 17-item Hamilton Rating Scale for Depression (HAM-D-17) and the Montgomery-Åsberg Depression Rating Scale (MADRS). For subjects treated with Compound-1-BUP at the 1:8 and 1:1 dose ratios or placebo, mean (standard deviation) changes from baseline to day 7 in HAM-D-17 total scores were −5.0 (6.1), −6.7 (3.4), and −1.0 (4.2), respectively (p=0.032 for the 1:1 ratio versus placebo) and mean (SD) changes from baseline to day 7 in MADRS total scores were −8.5 (0.4), −11.4 (6.6), and −3.5 (5.8), respectively. See Tables B and C.

TABLE B

Comparison of treatment efficacy between placebo, Cohort A and Cohort B assessed by Hamilton Depression Rating Sacle-17 (Total Score)

| Parameter | | Placebo (PBO) | Cohort A (1:8) | Cohort B (1:1) |
|---|---|---|---|---|
| Baseline score | # subjects | N = 4 | N = 14 | N = 14 |
| | mean (SD) | 19.0 (3.2) | 17.5 (2.0) | 19.4 (2.7) |
| | median | 18.5 | 17.5 | 19.0 |
| Change from baseline at Day 7 | # subjects | N = 4 | N = 13 | N = 13 |
| | mean (SD) | −1.0 (4.2) | −5.0 (6.1) | −6.7 (3.4) |
| | median | 0 | −4.0 | −6.0 |

| | Comparison of changes from baseline | |
|---|---|---|
| | Cohort A vs. PBO | Cohort B vs. PBO |
| mean (SD) | −4 (5.78) | −5.69 (3.57) |
| P value* | 0.337 | 0.032 |

*p value from exact Wilcoxon test
Cohort A: 1:8 ratio of Compound 1:Buprenorphine (0.25 mg:2 mg for days 1 to 3 and 0.5 mg:4 mg for days 4 to 7)
Cohort B: 1:1 ratio of Compound 1:Buprenorphine (4 mg:4 mg for days 1 to 3 and 8 mg:8 mg for days 4 to 7).

TABLE C

Comparison of treatment efficacy between placebo, Cohort A and Cohort B assessed by Montgomery-Åsberg Depression Rating Scale (Total Score)

| Parameter | | Placebo | Cohort A (1:8) | Cohort B (1:1) |
|---|---|---|---|---|
| Baseline score | # subjects | N = 4 | N = 14 | N = 14 |
| | mean (SD) | 24.5 (7.9) | 23.3 (4.1) | 26.4 (4.4) |
| | Median | 26.0 | 23.5 | 26.0 |
| Change from baseline at Day 7 | # subjects | N = 4 | N = 13 | N = 13 |
| | mean (SD) | −3.5 (5.8) | −8.5 (7.4) | −11.4 (6.6) |
| | median | −2.5 | −9.0 | −13.0 |

| | Comparison of changes from baseline | |
|---|---|---|
| | Cohort A vs. PBO | Cohort B vs. PBO |
| mean (SD) | −4.96 (7.10) | −7.88 (6.41) |
| P value* | 0.256 | 0.054 |

Cohort A: 1:8 ratio of Compound 1:Buprenorphine (0.25 mg:2 mg for days 1 to 3 and 0.5 mg:4 mg for days 4 to 7)
Cohort B: 1:1 ratio of Compound 1:Buprenorphine (4 mg:4 mg for days 1 to 3 and 8 mg:8 mg for days 4 to 7).

Visual analog scales (VAS) were used to assess drug liking and other subjective drug effects. Subjects on active drug at the 1:8 ratio experienced greater subjective experiences of "Feeling High" (Table D) and "Feeling Sedated" (Table E) compared to the 1:1 ratio. The VAS results are reported as predose and postdose scores showing the magnitude of difference in the subjective experiences. For example, on Day 7, the predose Cohort A VAS score for "Feeling High" was 5.8 and postdose score was 32.9, showing a difference of 27.1 score before and after dosing. In case of Cohort B, the predosing VAS score was 14.5 and postdosing was 19.6 showing only an increase of 5.1. The comparison between the two cohorts shows that Cohort A experienced a significant increase in "Feeling High" after the dosing compared to Cohort B.

TABLE D

Visual analog scale (VAS) results for "feeling high"

| Timepoint | | Placebo (mean[SD]) | Cohort A (1:8) (mean[SD]) | Cohort B (1:1) (mean[SD]) |
|---|---|---|---|---|
| Day 1 | Predose | 18.0 (20.98) | 8.6 (19.58) | 9.1 (13.70) |
| | Postdose | 48.0 (32.04) | 54.4 (36.63) | 29.4 (30.87) |
| Day 2 | Predose | 6.8 (4.65) | 14.8 (16.97) | 22.5 (23.63) |
| | Postdose | 9.0 (8.76) | 39.3 (29.40) | 31.5 (29.02) |
| Day 3 | Predose | 7.3 (2.63) | 7.2 (11.35) | 22.7 (27.21) |
| | Postdose | 6.3 (8.66) | 41.8 (30.31) | 35.5 (32.42) |
| Day 4 | Predose | 6.3 (4.92) | 10.2 (9.94) | 17.5 (22.92) |
| | Postdose | 7.8 (10.97) | 57.1 (30.21) | 19.1 (23.19) |
| Day 5 | Predose | 7.3 (10.59) | 6.3 (4.52) | 15.7 (20.68) |
| | Postdose | 23.8 (33.05) | 35.1 (34.95) | 19.5 (27.58) |
| Day 6 | Predose | 22.8 (25.68) | 4.6 (3.29) | 15.5 (21.99) |
| | Postdose | 29.3 (32.35) | 43.7 (30.21) | 22.1 (30.36) |
| Day 7 | Predose | 24.5 (26.85) | 5.8 (5.37) | 14.5 (23.57) |
| | Postdose | 9.0 (8.76) | 32.9 (30.14) | 19.6 (29.51) |

TABLE E

Visual analog scale (VAS) results for "feeling sedated"

| Timepoint | | Placebo (mean[SD]) | Cohort A (1:8) (mean[SD]) | Cohort B (1:1) (mean[SD]) |
|---|---|---|---|---|
| Day 1 | Predose | 5.3 (9.24) | 17.5 (26.98) | 3.0 (4.96) |
| | Postdose | 36.5 (38.73) | 60.4 (28.73) | 34.3 (31.51) |
| Day 2 | Predose | 5.5 (6.61) | 11.5 (12.80) | 13.8 (15.42) |
| | Postdose | 6.3 (6.75) | 48.9 (28.69) | 37.8 (31.21) |
| Day 3 | Predose | 5.5 (5.32) | 8.2 (8.64) | 21.6 (27.76) |
| | Postdose | 4.5 (3.87) | 49.0 (32.63) | 31.2 (29.48) |
| Day 4 | Predose | 5.8 (6.02) | 12.2 (15.80) | 22.4 (25.55) |
| | Postdose | 2.8 (2.22) | 38.4 (34.01) | 22.2 (24.54) |
| Day 5 | Predose | 4.0 (3.56) | 9.5 (13.69) | 13.9 (18.05) |
| | Postdose | 30.0 (34.55) | 37.0 (31.65) | 20.2 (23.79) |
| Day 6 | Predose | 9.8 (14.93) | 6.5 (5.68) | 10.6 (14.65) |
| | Postdose | 21.3 (25.62) | 44.8 (31.26) | 19.5 (24.77) |
| Day 7 | Predose | 10.8 (10.53) | 17.0 (21.21) | 9.7 (12.91) |
| | Postdose | 5.3 (3.77) | 30.3 (25.12) | 14.5 (24.22) |

Bioanalytical method used for determining the $C_{max}$ for Compound-1: A method was validated for measuring Compound-1 in human plasma (K2EDTA). Samples were analyzed using a 50 μL aliquot volume and a protein-precipitation extraction procedure followed by liquid chromatography/tandem mass spectrometry (LC/MS/MS). Compound-1 concentrations were calculated with a $1/x^2$ linear regression over a concentration range of 0.250 to 100 ng/mL using naltrexone-d3 as an internal standard. Ten-fold dilution was successfully tested at 400 ng/mL for both analytes. The API 5000 was operated in the Selected Reaction Monitoring (SRM) mode under optimized conditions for detection of Compound-1, naltrexone-d3 positive ions formed by electrospray ionization.

Bioanalytical method used for determining the $C_{max}$ for buprenorphine: A method was validated for measuring buprenorphine in human plasma (K2EDTA). Samples were analyzed using a 400 μL aliquot volume and a solid-phase extraction procedure followed by liquid chromatography/tandem mass spectrometry (LC/MS/MS). Buprenorphine concentrations were calculated with a $1/x^2$ linear regression over a concentration range of 0.250 to 100 ng/mL. The API 5000 was operated in the Selected Reaction Monitoring (SRM) mode under optimized conditions for detection of buprenorphine and buprenorphine-$d_4$ positive ions formed by electrospray ionization.

The [$^{35}$S]GTPγS assay measures the functional properties of a compound by quantifying the level of G-protein activation following agonist binding in studies using stably transfected cells, and is considered to be a measure of the efficacy of a compound. Membranes from CHO (Chinese Hamster Ovary) cells that stably expressed the cloned human μ opioid receptor were used in the experiments. In a final volume of 0.5 mL, 12 different concentrations of Compound-1 were incubated with 7.5 μg of CHO cell membranes that stably expressed the human μ opioid receptor. The assay buffer consisted of 50 mM Tris-HCl, pH 7.4, 3 mM $MgCl_2$, 0.2 mM EGTA, 3 μM GDP, and 100 mM NaCl. The final concentration of [35S]GTPγS was 0.080 nM. Nonspecific binding was measured by inclusion of 10 μM GTPγS. Binding was initiated by the addition of the membranes. After an incubation of 60 min at 30° C., the samples were filtered through Schleicher & Schuell No. 32 glass fiber filters. The filters were washed three times with cold 50 mM Tris-HCl, pH 7.5, and were counted in 2 mL of Ecoscint scintillation fluid. Data are the mean Emax and $EC_{50}$ values±S.E.M. For calculation of the Emax values, the basal [35S]GTPγS binding was set at 0%, and the 100% [35S]GTPγS binding level was set at the maximum binding achieved with DAMGO.

Example 2

Experiments were conducted in rats to assess the ability of opioid antagonists to modulate buprenorphine-induced dopamine efflux in the Nucleus Accumbens shell (NAc-sh) region of the mesolimbic region of the brain. Male rats weighing 300-400 grams were used for all studies. To measure the efflux of dopamine in the NAc-sh an in vivo microdialysis method was utilized in free-moving rats. This method allows the sampling of extracellular cerebrospinal fluid (C SF) from specific brain regions of interest and measurement of neurotransmitter concentrations following the analysis of sampled dialysate with HPLC-EC.

Each rat underwent surgical implantation of microdialysis guide cannula (CMA 12, CMA Microdialysis) to guide the insertion of the microdialysis probe later on. Rats were anesthetized with a mixture of ketamine/xylazine (80/6 mg/kg IP) and placed in a stereotaxic apparatus. Using bregma and skull as reference points, final coordinates were determined by The Rat Brain in Stereotaxic Coordinates (Paxinos and Watson, 2006) for the nucleus accumbens shell (+1.7 A/P, +−0.80 M/L, −7.8 D/V) and the guide cannula were lowered vertically into position (D/V=−5.8 from the skull) and fixed to the skull with glass-ionomer dental acrylic. Guide cannula were capped with dummy probes until microdialysis probe insertion. On the day prior to experimentation (3-4 days post-surgery), animals were weighed to determine appropriate dose for test articles. A microdialysis probe (CMA 12, 2 mm membrane, CMA microdialysis) was then inserted through the guide cannula. Microdialysis probes were connected to a tether system allowing free movement and sterile artificial CSF (aCSF) (CMA microdialysis) was pumped via microsyringe pumps at a rate of 0.25 μL/min through the probe overnight for approximately 16 hours prior to experimentation. On the day following probe insertion, sterile aCSF perfusion was increased to 2.0 μl/min and a pre-baseline equilibration period was established for at least 1.5 hours prior to initiating continuous collection of CSF. After the equilibration period a baseline neurotransmitter levels were determined for each animal over 1.75 hours. Following this baseline period, antagonist plus buprenonphine (0.1 mg/kg, SC)

were administered and continuous sampling of the microdialysate conducted for an additional 4.25 hours. While continuously collected, the CSF was automatically fractioned into 15 minute periods using a chilled microfraction collector for the entire 6.0 hours collection period (1.75 baseline phase and 4.25 hour treatment phase). Each sample was analyzed via HPLC-EC to determine neurotransmitter concentration of dopamine based upon a six-point standard curve. The average dopamine per sample over the 4.25 treatment phase was used in all comparisons among treatment groups.

Figure 1:
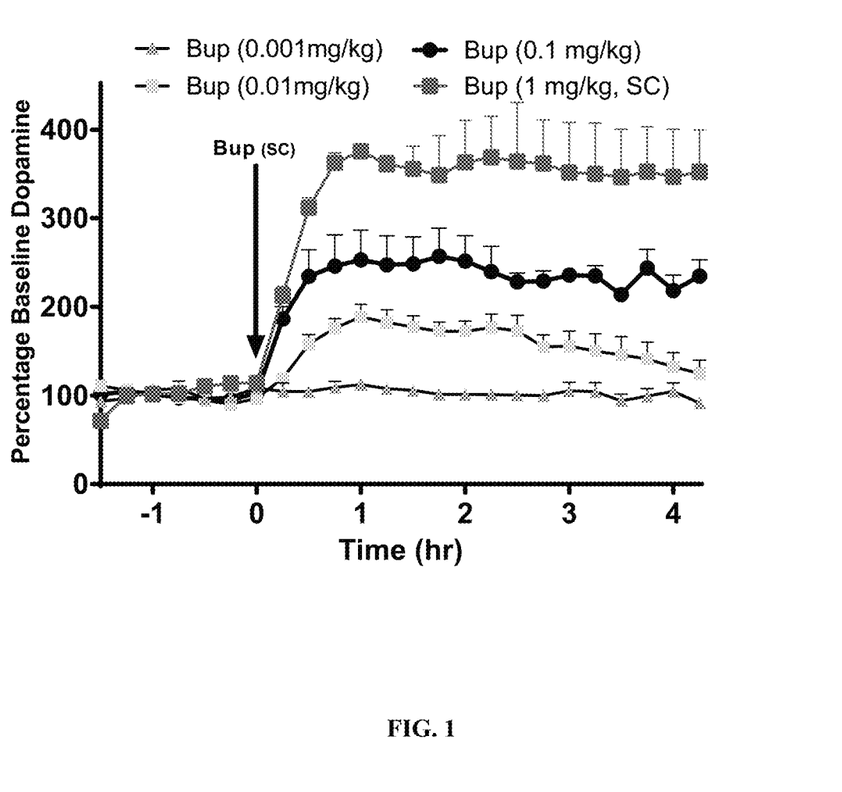
FIG. 1: Efflux of dopamine in nucleus accumbens shell after administration of buprenorphine at 0.001 mg/kg, 0.01 mg/kg, 0.1 mg/kg and 1 mg/kg doses after subcutaneous (SC) administration.
Figure 2:
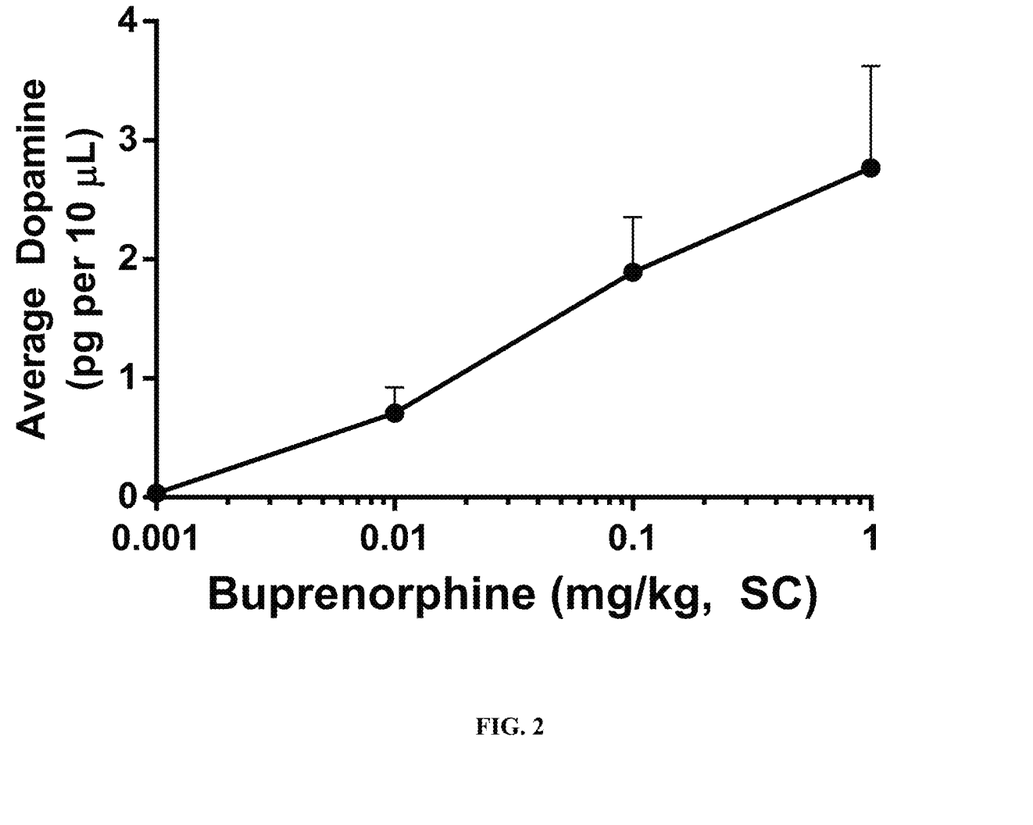
FIG. 2: Dopamine efflux following (SC) administration of buprenorphine at increasing doses.
Figure 3:
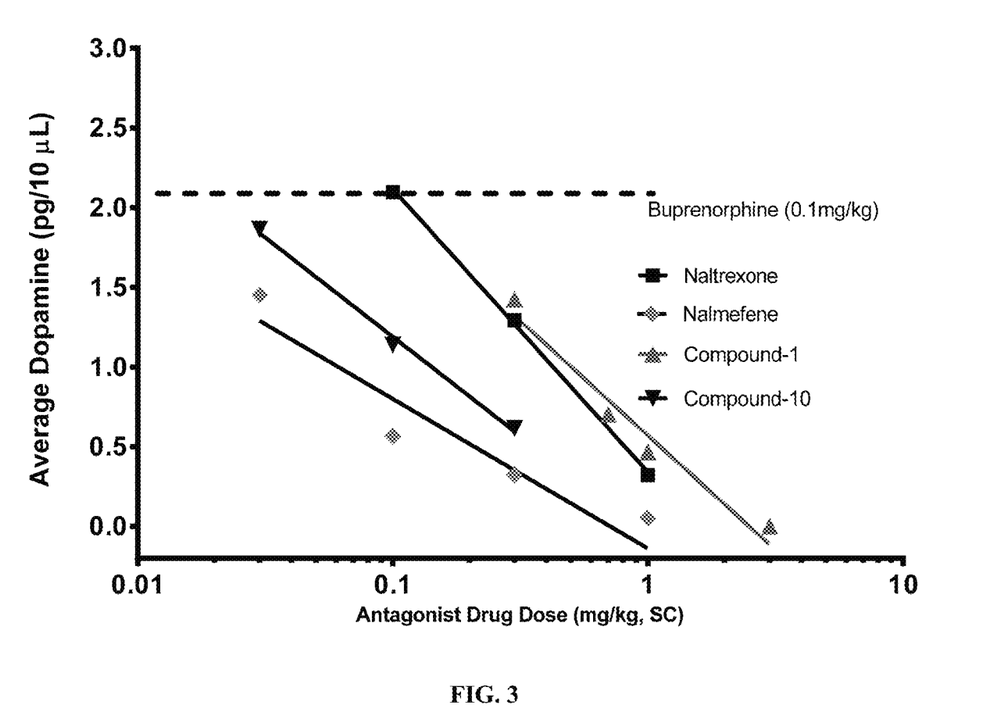
FIG. 3: Reduction in the efflux of dopamine in nucleus accumbens shell following administration of Compound-1, Compound-10, naltrexone and nalmefene with Buprenorphine (0.1 mg/kg).
Figure 4:
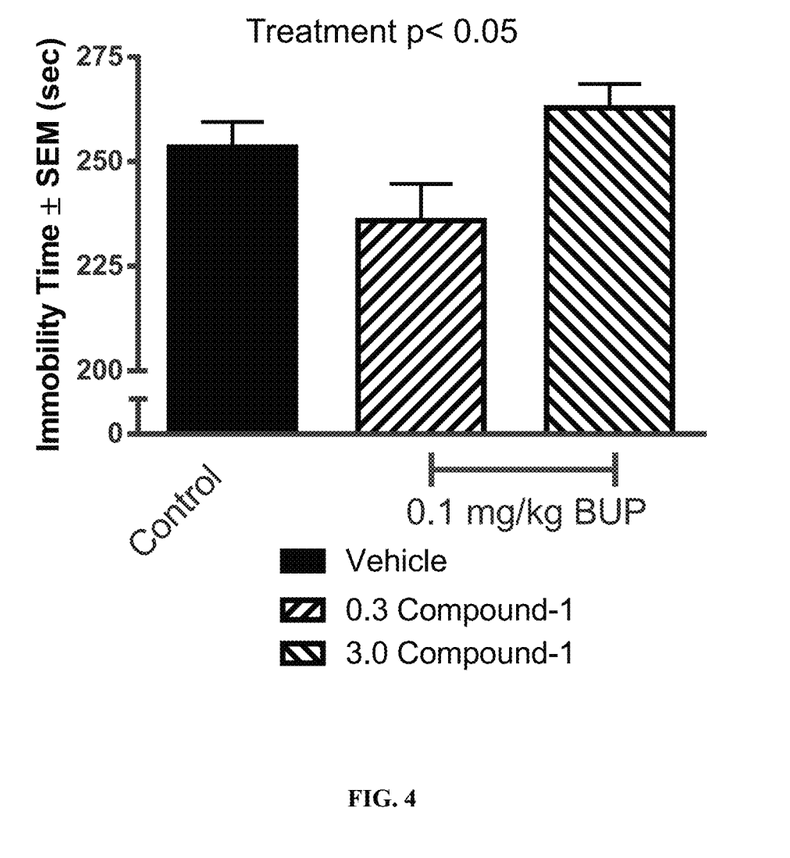
FIG. 4: Increase in immobility following increased concentrations of Compound-1 in forced swim test in WKY rats treated with Buprenorphine (0.1 mg/kg).

In rats buprenorphrine resulted in a dose dependent increases in NAc-sh dopamine efflux between doses of 0.01 and 1 mg per kg (FIGS. 1 and 2). At doses of 0.1 and 1.0 mg per kg behavioral effects of buprenorphine were observed, including initial sedation followed by hyperactivity. Consequently all additional experiments with μ opioid antagonist used a dose of 0.1 mg per kg of buprenorphine since it represented the lowest dose associated with clear behavioral effects. As shown in FIG. 3 each of the four antagonists evaluated resulted in linear dose-dependent decreases in NAc-sh dopamine efflux.

Example 3

Due to the inherent minor stress associated with PK sampling, and the sensitivity of neural chemistry to this stress, different groups of animals were required to establish circulating concentrations of buprenorphine and the antagonists at each dose level evaluated Male rats weighing between 300-400 grams, the same weight range used in the microdialysis studies, were used for. Since all animals received a fixed dose of buprenorphine, a commercial formulation of buprenorphine (Buprenex (Reckitt Benckiser)) was diluted to 0.1 mg/ml with sterile saline and then used as the vehicle for the required doses of compound 1, Compound-10, naltrexone and nalmefene. This approached ensured that at each dose of the antagonist studied the concomitant dose of buprenorphrine would be 0.1 mg per kg. All injections were made by the subcutaneous route at the doses indicated in Table G. Sterile solutions of the test formulations (combination of antagonist with 0.1 mg/kg buprenorphine) were given subcutaneously (designated as time 0). Sample of blood were collected at 5, 15, 30, 60 and 120 minutes post dosing. For each blood sampling time point, rats were lightly anesthetized using (3%) isoflourane anesthesia and approximately 200 μl of blood was withdrawn from the lateral tail vein using a 27.5 gauge needle and placed into chilled K2 EDTA tubes. The collection tubes were inverted 10-15 times and then held on ice prior to centrifugation. Plasma was obtained by centrifuging samples for 2 minutes at 14,000×g (11,500 RPM using Eppendorf 5417R centrifuge rotor) at 4° C. The harvested samples of plasma were frozen at −80° C. until assayed for buprenorphine and the antagonists (Compound 1, Compound 10, naltrexone or nalmefene). The $C_{max}$ values for each antagonist at the doses evaluated are shown in Table F.

TABLE F $C_{max}$ values for Compound-1, Compound-10, naltrexone and nalmefene with Buprenorphine (0.1 mg/kg)

| | Dose of Antagonist mg per kg | | | |
|---|---|---|---|---|
| Antagonist | 0.03 | 0.1 | 0.3 | 1.0 |
| Compound-1 | — | — | 11.8 | 75.5 |

TABLE F-continued $C_{max}$ values for Compound-1, Compound-10, naltrexone and nalmefene with Buprenorphine (0.1 mg/kg)

| | Dose of Antagonist mg per kg | | | |
|---|---|---|---|---|
| Compound-10 | 2.24 | 18.1 | 29.5 | — |
| Naltrexone | — | 19.27 | 76.9 | 169 |
| Nalmefene | — | 14.13 | 25.6 | 162 |

Example 4

Figure 5:
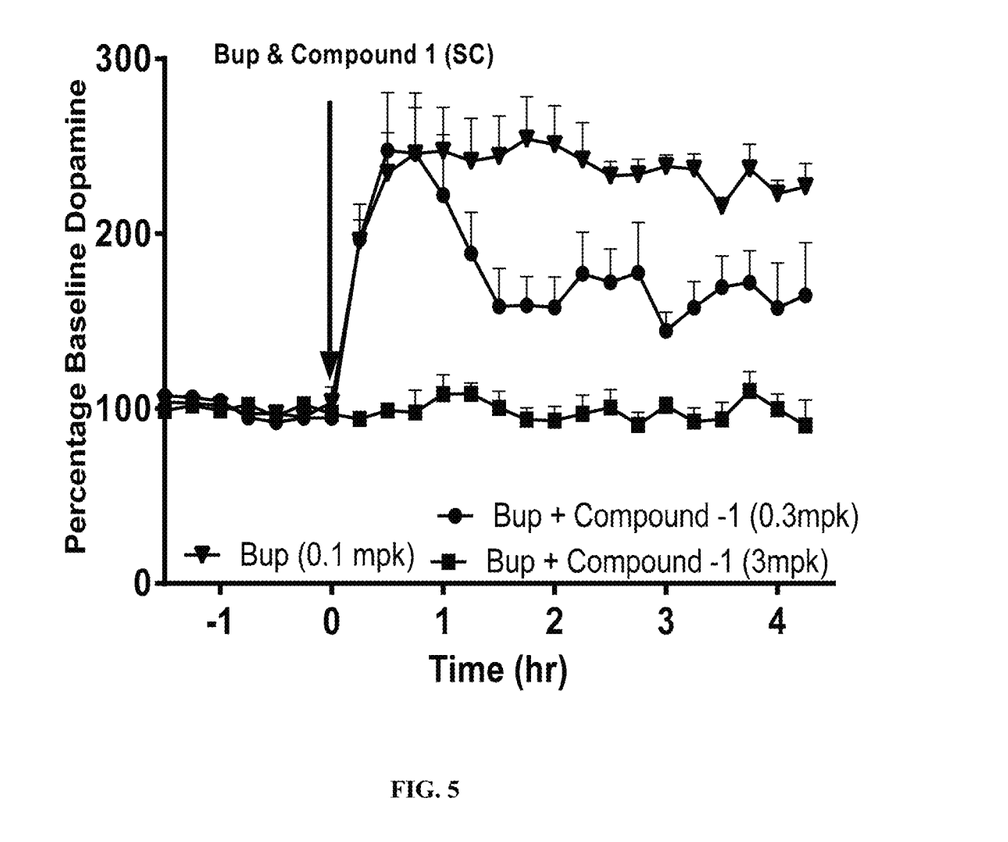
FIG. 5: The effect of Compound-1 on dopamine efflux in WKY rats undergoing forced swim test after treatment with Buprenorphine (0.1 mg/kg).
Figure 6:
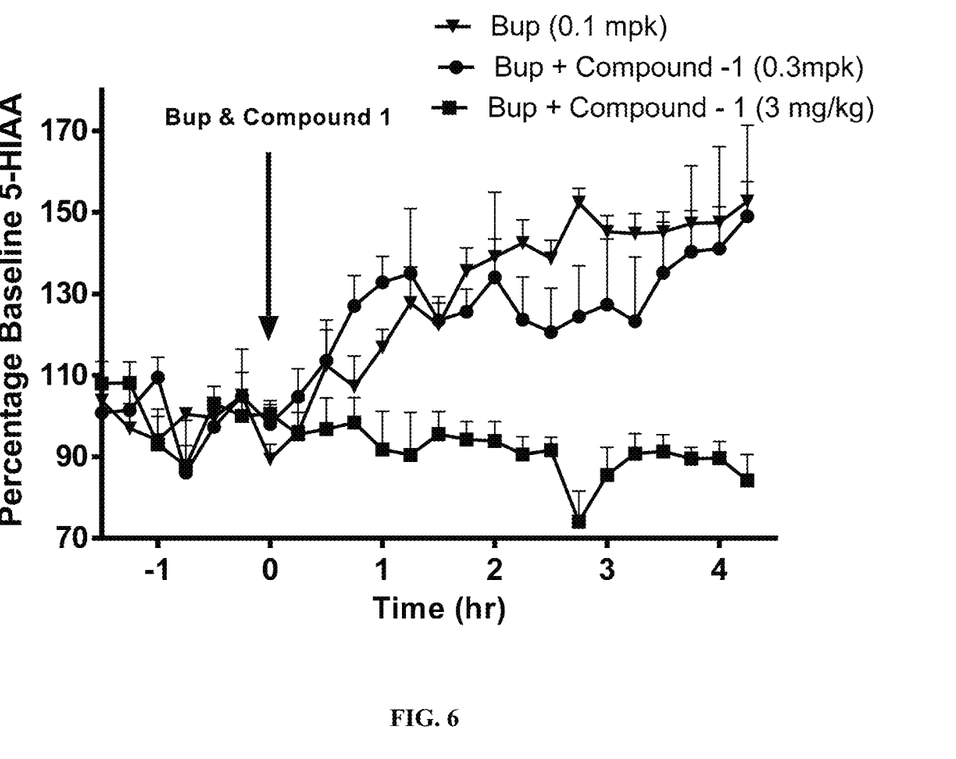
FIG. 6: The effect of Compound 1 on 5-Hydroxyindoleacetic acid (5-HIAA) release in WKY rats undergoing the forced swim test after treatment with Buprenorphine (0.1 mg/kg).

In the "forced swim test" (FST) rats are placed in a tank of water, from which they cannot escape, on two successive days; 15 minutes on the first day and 5 minutes on the second day. While in the water they will swim, attempt to climb the container wall or become "immobile" floating in the water. The total time rats are immobility increases between the first and second day. Drugs that have antidepressant effects in humans reduce immobility time on day 2 and this model is frequently used to evaluate potential anti-depressive like activity of drugs. Strain of rat can also affect total immobility time, with the Wistar-Kyoto (WKY) strain showing high immobility times. The WKY rat is spontaneously hypertensive and displays hormonal and depressive-like behavioral abnormalities. Rats received three separate subcutaneous injections of either vehicle alone or a combination of buprenorphine (0.1 mg/kg) and Compound-1 (0.3 or 3.0 mg/kg) at 1, 19, and 23 h after the first exposure to the swim tanks. At 24 h after the first swim, rats were retested for 5 minutes. Videos were scored manually for immobility time (in seconds) using a manual stop watch in 60 second intervals by a rater blinded to the treatment groups. A rat was judged to be immobile if it was making only movements necessary to keep its head above water. Results for this study are shown in FIG. 5. Immobility time was significantly lower (p<0.05) in rats given the combination of buprenorphine and Compound 1 at 0.3 mg/kg, indicating an anti-depressive like action.

While this invention has been particularly shown and described with references to preferred embodiments thereof, it will be understood by those skilled in the art that various changes in form and details may be made therein without departing from the scope of the invention encompassed by the appended claims.

What is claimed is:

1. A composition comprising a pharmaceutically effective amount of buprenorphine and Compound-1:

in a solid dosage form for oral administration.

2. The composition of claim 1, wherein said solid dosage form is selected from the group consisting of capsule, tablet, pill, powder, and granule.

3. The composition according to claim 2, wherein said solid dosage form is a tablet.

4. The composition according to claim 1, wherein the molar ratio of Compound-1:buprenorphine is about 0.5-5.0:1.0.

5. The composition according to claim 4, wherein the molar ratio of Compound-1:buprenorphine is about 0.5-4.0:1.0.

6. The composition according to claim 4, wherein the molar ratio of Compound-1:buprenorphine is about 0.5-3.0:1.0.

7. The composition according to claim 4, wherein the molar ratio of Compound-1:buprenorphine is about 0.5-2.5:1.0.

8. The composition according to claim 4, wherein the molar ratio of Compound-1:buprenorphine is about 0.5-1.75:1.0.

9. The composition according to claim 1, further comprising an additional agent selected from a selective serotonin re-uptake inhibitor (SSRI), serotonin reuptake inhibitor, serotonin-norepinephrine reuptake inhibitor (SNRI), monoamine oxidase inhibitor (MAOIs) and tricyclic antidepressants, or an antidepressant compound belonging to the heterocyclic class.

10. The composition of claim 9, wherein said additional anti-depressant is selected from fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, femoxetine and alaproclate.

11. The composition according to claim 4, wherein the molar ratio of Compound-1:buprenorphine is about 0.75-1.5:1.0.

12. The composition according to claim 4, wherein the molar ratio of Compound-1:buprenorphine is about 0.9-1.3:1.0.

13. A method of treating a depressive disorder comprising administering, to a patient in need thereof, Compound-1 and buprenorphine in solid dosage form for oral administration.

14. The method according to claim 13, wherein said depressive disorder is selected from major depressive disorder, chronic depression, severe unipolar recurrent major depressive episodes, dysthymic disorder, depressive neurosis and neurotic depression, melancholic depression, atypical depression, reactive depression, treatment resistant depression, seasonal affective disorder and pediatric depression; premenstrual syndrome, premenstrual dysphoric disorder, hot flashes, bipolar disorders or manic depression, bipolar I disorder, bipolar II disorder and cyclothymic disorder.

15. The method according to claim 14, wherein said depressive disorder is major depressive disorder.

16. The method according to claim 15, wherein said major depressive disorder is resistant to two or more antidepressants.

17. The method according to claim 16, wherein the antidepressants are selected from the group comprising selective serotonin reuptake inhibitors (SSRIs), Serotonin-norepinephrine reuptake inhibitors (SNRIs), Monoamine oxidase inhibitors (MAOIs) and Tricyclic antidepressants.

18. The method according to claim 13, wherein said depressive disorder is treatment resistant depression.

19. The method according to claim 13, wherein said subject exhibits one or more depressive symptoms selected from irritability, feelings of hopelessness and helplessness, inability to concentrate, sadness, insomnia, appetite loss, lack of interest in life's activities, thoughts of suicide, dizziness, nausea, vomiting, hyperhidrosis, menorrhagia, pain in extremity, constipation, sedation, fatigue, feeling abnormal, flushing and somnolence.

20. The method according to claim 13, wherein the molar ratio of Compound-1:buprenorphine is about 0.5-5.0:1.0.

21. The method according to claim 13, wherein said solid dosage form is selected from the group consisting of capsule, tablet, pill, powder, and granule.

22. The composition according to claim 21, wherein said solid dosage form is a tablet.

23. The method according to claim 20, wherein the molar ratio of Compound-1:buprenorphine is about 0.5-4.0:1.0.

24. The method according to claim 20, wherein the molar ratio of Compound-1:buprenorphine is about 0.5-3.0:1.0.

25. The method according to claim 20, wherein the molar ratio of Compound-1:buprenorphine is about 0.5-2.5:1.0.

26. The method according to claim 20, wherein the molar ratio of Compound-1:buprenorphine is about 0.5-1.75:1.0.

27. The method according to claim 20, wherein the molar ratio of Compound-1:buprenorphine is about 0.75-1.5:1.0.

28. The method according to claim 20, wherein the molar ratio of Compound-1:buprenorphine is about 0.9-1.3:1.0.

29. The method according to claim 13, wherein the solid dosage form further comprises an additional agent for the treatment of depression selected from a selective serotonin re-uptake inhibitor, serotonin reuptake inhibitor (SSRI), serotonin-norepinephrine reuptake inhibitor (SNRI), monoamine oxidase inhibitor (MAOIs) and tricyclic antidepressants, or an antidepressant compound belonging to the heterocyclic class.

30. The composition of claim 29, wherein said additional anti-depressant is selected from fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, femoxetine and alaproclate.

31. A method of treating pain comprising administering, to a patient in need thereof, pharmaceutically effective amounts of Compound-1 and buprenorphine in solid dosage form for oral administration.

32. The method according to claim 31, wherein the pain is selected from moderate to severe cancer pain, moderate to severe post-surgical pain, pain following physical trauma, pain associated with cardiac infarction and inflammatory pain.

33. The method according to claim 31, wherein said solid dosage form is selected from the group consisting of capsule, tablet, pill, powder, and granule.

34. The composition according to claim 33, wherein said solid dosage form is a tablet.

35. The method according to claim 31, wherein the molar ratio of Compound-1:buprenorphine is about 0.5-5.0:1.0.

36. The method according to claim 35, wherein the molar ratio of Compound-1:buprenorphine is about 0.5-4.0:1.0.

37. The method according to claim 35, wherein the molar ratio of Compound-1:buprenorphine is about 0.5-3.0:1.0.

38. The method according to claim 35, wherein the molar ratio of Compound-1:buprenorphine is about 0.5-2.5:1.0.

39. The method according to claim 35, wherein the molar ratio of Compound-1:buprenorphine is about 0.5-1.75:1.0.

40. The method according to claim 35, wherein the molar ratio of Compound-1:buprenorphine is about 0.75-1.5:1.0.

41. The method according to claim 35, wherein the molar ratio of Compound-1:buprenorphine is about 0.9-1.3:1.0.

\* \* \* \* \*